United States Patent
Hong et al.

(10) Patent No.: US 11,578,081 B1
(45) Date of Patent: Feb. 14, 2023

(54) CRYSTAL FORM AS INHIBITOR OF ACC1 AND ACC2, AND PREPARATION METHOD THEREFOR AND USE THEREOF

(71) Applicants: ZHANGZHOU PIEN TZE HUANG PHARMACEUTICAL CO., LTD., Fujian (CN); MEDSHINE DISCOVERY INC., Jiangsu (CN)

(72) Inventors: Fei Hong, Zhangzhou (CN); Jinming Huang, Zhangzhou (CN); Jinxia Lin, Zhangzhou (CN); Yichao Zhuang, Zhangzhou (CN); Zhiyi Luo, Zhangzhou (CN); Xiaoping Zheng, Shanghai (CN); Zhigan Jiang, Shanghai (CN); Haiying He, Shanghai (CN)

(73) Assignees: ZHANGZHOU PIEN TZE HUANG PHARMACEUTICAL CO., LTD., Fujian (CN); MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 17/781,839

(22) PCT Filed: Dec. 4, 2020

(86) PCT No.: PCT/CN2020/133892
§ 371 (c)(1),
(2) Date: Jun. 2, 2022

(87) PCT Pub. No.: WO2021/110135
PCT Pub. Date: Jun. 10, 2021

(30) Foreign Application Priority Data

Dec. 5, 2019 (CN) .......................... 201911235373.6

(51) Int. Cl.
*C07D 495/04* (2006.01)

(52) U.S. Cl.
CPC ........ *C07D 495/04* (2013.01); *C07B 2200/13* (2013.01)

(58) Field of Classification Search
CPC combination set(s) only.
See application file for complete search history.

(56) References Cited

U.S. PATENT DOCUMENTS

| 2016/0108060 A1 | 4/2016 | Greenwood et al. |
| 2016/0108061 A1 | 4/2016 | Greenwood et al. |

(Continued)

FOREIGN PATENT DOCUMENTS

| CN | 105358152 A | 2/2016 |
| CN | 105358154 A | 2/2016 |

(Continued)

OTHER PUBLICATIONS

International Search Report (English and Chinese) and Written Opinion of the International Searching Authority (English and Chinese) issued in PCT/CN2020/133892, dated Feb. 25, 2021; ISA/CN.
Priority text: Chinese Patent Application No. 2019112353736, filed Dec. 5, 2019 (not published).
Aug. 5, 2022 Extended European Search Report issued in International Patent Application No. PCT/CN2020133892.

*Primary Examiner* — Valerie Rodriguez-Garcia
(74) *Attorney, Agent, or Firm* — Harness, Dickey & Pierce, P.L.C.

(57) ABSTRACT

Disclosed are a crystal form (I) as an inhibitor of ACC1 and ACC2, a preparation method therefor, and the use thereof in the preparation of a drug as an inhibitor of ACC1 and ACC2.

(Continued)

(56) References Cited

U.S. PATENT DOCUMENTS

| | | | |
|---|---|---|---|
| 2019/0225623 | A1 | 7/2019 | Alexander et al. |
| 2019/0330224 | A1 | 10/2019 | Ghosh et al. |
| 2020/0199147 | A1 | 6/2020 | Geier et al. |
| 2021/0238190 | A1 | 8/2021 | Zheng et al. |

FOREIGN PATENT DOCUMENTS

| | | | |
|---|---|---|---|
| CN | 108368125 A | | 8/2018 |
| CN | 108699078 A | | 10/2018 |
| CN | 110382503 A | | 10/2019 |
| CN | 112218871 A | | 1/2021 |
| WO | 2013071169 A1 | | 5/2013 |
| WO | 2017147161 A1 | | 8/2017 |
| WO | WO2017/147161 | * | 8/2017 |
| WO | 2019233443 A1 | | 12/2019 |
| WO | WO2019/233443 | * | 12/2019 |

\* cited by examiner

8 Claims, 2 Drawing Sheets

(I)

CRYSTAL FORM AS INHIBITOR OF ACC1 AND ACC2, AND PREPARATION METHOD THEREFOR AND USE THEREOF

CROSS-REFERENCE TO RELATED APPLICATIONS

This application is a U.S. National Phase Application under 35 U.S.C. 371 of International Application No. PCT/CN2020/133892, filed on Dec. 4, 2020, which claims the benefit of Chinese Patent Application No. 201911235373.6, filed on Dec. 5, 2019. The entire disclosures of the above applications are incorporated herein by reference.

TECHNICAL FIELD

The present disclosure relates to a crystal form as an inhibitor of ACC1 and ACC2, a preparation method therefor, and the use thereof in the preparation of a drug as an inhibitor of ACC1 and ACC2.

BACKGROUND

Fatty acid metabolism disorder caused by increased fatty acid synthesis, decreased fatty acid oxidation, or both is a sign of various metabolic disorders, including insulin resistance, hepatic steatosis, dyslipidemia, obesity, metabolic syndrome (MetSyn), non-alcoholic fatty liver disease (NAFLD), etc. In addition, fatty acid metabolism disorder may lead to the development of type 2 diabetes mellitus (T2DM), non-alcoholic steatohepatitis (NASH), atherosclerosis and other vascular diseases. Fatty acid metabolism disorder is also a sign of cancer, which may lead to abnormal and persistent proliferation of malignant tumor cells. Therefore, inhibiting fatty acid synthesis and/or stimulating fatty acid oxidative metabolism may be beneficial to these diseases (PNAS, 2016, E1796-E1805).

Acetyl-CoA carboxylase (ACC) catalyzes the conversion of acetyl-CoA to malonyl-CoA, which is the first step in fatty acid synthesis, and is also the rate-determining step. There are two subtypes of ACC, namely ACC1 and ACC2. ACC1 is mainly distributed in liver and adipose tissue, while ACC2 is mainly distributed in liver, heart and muscle tissue. In the liver, the malonyl-CoA formed by catalysis of ACC1 in the cytoplasm is mainly responsible for the synthesis and elongation of fatty acids; the malonyl-CoA formed by catalysis of ACC2 on the surface of mitochondria mainly regulates the oxidative metabolism of fatty acids by inhibiting a carnitine transferase I (PNAS, 2016, E1796-E1805). Therefore, inhibiting the two subtypes of ACC simultaneously may reduce fatty acid synthesis and stimulate fatty acid oxidative metabolism.

WO 2013071169 A1 discloses the use of an ACC inhibitor I-181 in the treatment of related diseases.

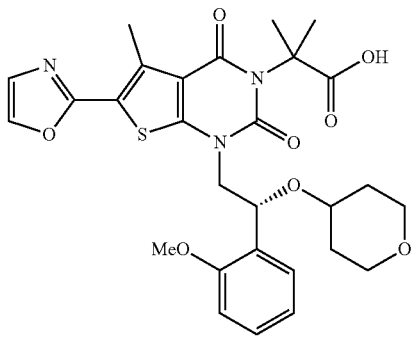

I-180

CONTENT OF THE PRESENT INVENTION

The present disclosure provides a crystal form A of a compound of formula (I), wherein the crystal form has an X-ray powder diffraction pattern comprising characteristic diffraction peaks at the following 2θ angles: 8.54±0.20°, 17.64±0.20° and 24.81±0.20°;

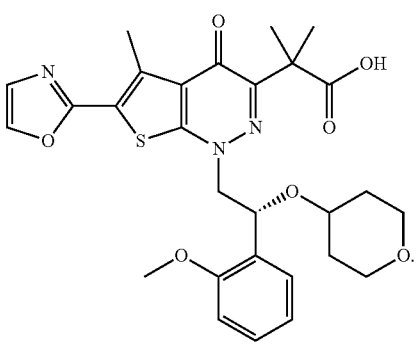

(I)

In some embodiments of the present disclosure, the above-mentioned crystal form A of the compound of formula (I) has an X-ray powder diffraction pattern comprising characteristic diffraction peaks at the following 2θ angles: 8.54±0.20°, 10.87±0.20°, 15.55±0.20°, 16.56±0.20°, 17.64±0.20°, 21.32±0.20°, 23.53±0.20° and 24.81±0.20°.

In some embodiments of the present disclosure, the above-mentioned crystal form A of the compound of formula (I) has an X-ray powder diffraction pattern comprising characteristic diffraction peaks at the following 2θ angles: 6.91°, 8.54°, 8.80°, 9.51°, 10.87°, 11.30°, 12.38°, 12.81°, 13.84°, 14.10°, 15.55°, 16.56°, 17.64°, 17.99°, 18.76°, 19.07°, 20.27°, 20.63°, 21.32°, 22.19°, 22.71°, 23.53°, 24.07°, 24.81°, 26.80°, 27.40°, 27.79°, 28.34°, 29.94°, 30.86°, 30.86°, 31.34°, 31.98°, 33.17°, 33.69°, 35.21°, 35.64°, 36.25°, 36.75°, 37.79° and 38.98°.

In some embodiments of the present disclosure, the above-mentioned crystal form A of the compound of formula (I) has an XRPD pattern as shown in FIG. 1.

In some embodiments of the present disclosure, the above-mentioned crystal form A has an XRPD pattern analysis data as shown in Table 1:

TABLE 1

The XRPD pattern analysis data of the crystal form A

| No. | 2θ angle (°) | Intensity | Relative intensity [%] | No. | 2θ angle (°) | Intensity | Relative intensity [%] |
|---|---|---|---|---|---|---|---|
| 1 | 6.91 | 615.79 | 6.80 | 21 | 22.71 | 709.64 | 7.83 |
| 2 | 8.54 | 2147.51 | 23.70 | 22 | 23.53 | 2707.12 | 29.87 |
| 3 | 8.80 | 2011.72 | 22.20 | 23 | 24.07 | 470.86 | 5.20 |
| 4 | 9.51 | 324.49 | 3.58 | 24 | 24.81 | 5799.41 | 64.00 |
| 5 | 10.87 | 1372.62 | 15.15 | 25 | 26.80 | 444.02 | 4.90 |
| 6 | 11.30 | 941.82 | 10.39 | 26 | 27.40 | 548.32 | 6.05 |
| 7 | 12.38 | 341.14 | 3.76 | 27 | 27.79 | 250.31 | 2.76 |
| 8 | 12.81 | 769.27 | 8.49 | 28 | 28.34 | 397.41 | 4.39 |
| 9 | 13.84 | 1010.70 | 11.15 | 29 | 29.94 | 192.52 | 2.12 |
| 10 | 14.10 | 610.77 | 6.74 | 30 | 30.86 | 286.85 | 3.17 |
| 11 | 15.55 | 1881.51 | 20.76 | 31 | 31.34 | 497.20 | 5.49 |
| 12 | 16.56 | 840.70 | 9.28 | 32 | 31.98 | 185.22 | 2.04 |
| 13 | 17.64 | 9061.51 | 100.00 | 33 | 33.17 | 165.37 | 1.83 |
| 14 | 17.99 | 748.47 | 8.26 | 34 | 33.69 | 109.90 | 1.21 |
| 15 | 18.76 | 192.99 | 2.13 | 35 | 35.21 | 377.04 | 4.16 |
| 16 | 19.07 | 1211.89 | 13.37 | 36 | 35.64 | 108.86 | 1.20 |
| 17 | 20.27 | 262.07 | 2.89 | 37 | 36.25 | 230.99 | 2.55 |
| 18 | 20.63 | 685.02 | 7.56 | 38 | 36.75 | 131.37 | 1.45 |
| 19 | 21.32 | 1725.07 | 19.04 | 39 | 37.79 | 183.21 | 2.02 |
| 20 | 22.19 | 276.64 | 3.05 | 40 | 38.98 | 165.44 | 1.83 |

In some embodiments of the present disclosure, the above-mentioned crystal form A has a differential scanning calorimetry curve comprising an endothermic peak with an onset at 234.9° C.

In some embodiments of the present disclosure, the above-mentioned crystal form A has a DSC pattern as shown in FIG. 2.

In some embodiments of the present disclosure, the above-mentioned crystal form A has a thermal gravimetric analysis curve showing a weight loss of 0.86% at 200.0° C.±3° C.

In some embodiments of the present disclosure, the above-mentioned crystal form A has a TGA pattern as shown in FIG. 3.

Technical Effects

The crystal form A of the compound of formula (I) in the present disclosure is stable, and less affected by light, heat and humidity; moreover, the compound of formula (I) and the crystal form A thereof in the present disclosure have good efficacy in vivo, and have a broad prospect for preparation of drugs.

DEFINITION AND DESCRIPTION

Unless otherwise stated, the following terms and phrases used herein are intended to have the following meanings. A specific phrase or term should not be considered uncertain or unclear unless specifically defined, but should be understood in an ordinary meaning. When a trade name appears herein, it is intended to refer to the corresponding commodity or an active ingredient thereof.

The intermediate compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The chemical reactions described in the specific embodiments of the present disclosure are completed in a suitable solvent, wherein the solvent must be suitable for the chemical changes of the present disclosure and the reagents and materials required thereby. In order to obtain the compounds of the present disclosure, sometimes a person skilled in the art needs to modify or select synthesis steps or reaction schemes based on the existing embodiments.

The present disclosure will be specifically described below by way of examples which are not intended to limit the present disclosure in any way.

All solvents used in the present disclosure are commercially available and can be used without further purification.

The solvents used in the present disclosure are commercially available. The present disclosure uses the following abbreviations: EtOH represents ethanol; MeOH represents methanol; TFA represents trifluoroacetic acid; TsOH represents p-toluenesulfonic acid; mp represents melting point; $EtSO_3H$ represents ethanesulfonic acid; $MeSO_3H$ represents methanesulfonic acid; THF represents tetrahydrofuran; EtOAc represents ethyl acetate; RuPhos represents 2-dicyclohexylphosphino-2',6'-diisopropoxybiphenyl; AcCl represents acetyl chloride; DCM represents dichloromethane; DMSO represents dimethyl sulfoxide.

Compounds are named by hand or ChemDraw® software, and commercially available compounds are named by the supplier catalog names.

The X-ray powder diffractometer (XRPD) method in the present disclosure

Instrument model: X'Pert³/Empyrean X-ray diffractometer from PANalytical

Test method: approximately 10 mg of the sample is used for XRPD detection.

The detailed XRPD parameters are as follows:
Ray source: Cu, kα (Kα1=1.540598 Å, Kα2=1.544426 Å, Kα2/Kα1 intensity ratio: 0.5)
Light tube voltage: 45 kV, light tube current: 40 mA
Divergence slit: fixed ⅛ deg
First soller slit: 0.04 rad, second soller slit: 0.04 rad
Receiving slit: none, anti-scatter slit: 7.5 mm
Measuring time: 5 min
Scanning angle range: 3-40 deg
Step width angle: 0.0263 deg (X'Pert³)/0.0167 deg (Empyrean)
Step length: 46.665 seconds (X'Pert³)/17.780 seconds (Empyrean)
Sample disk rotating speed: 15 rpm The differential scanning calorimeter (DSC) method used in the present disclosure Instrument model: TA Q2000/Discovery DSC 2500 differential scanning calorimeter Test method: a sample (about 1 to 5 mg) was taken and placed in a DSC aluminum pan for testing. The sample was heated from 25° C. (room temperature) until the decomposition of the sample at a heating rate of 10° C./min under the condition of 50 mL/min of $N_2$.

The thermal gravimetric analyzer (TGA) method used in the present disclosure

Instrument model: TA Discovery TGA 5500 thermal gravimetric analyzer

Test method: a sample (about 1 to 5 mg) was taken and placed in a TGA aluminum pan for testing. The sample was heated from room temperature to 350° C. at a heating rate of 10° C./min under the condition of 10 mL/min of $N_2$.

DETAILED DESCRIPTION OF THE PREFERRED EMBODIMENT

Figure 1:
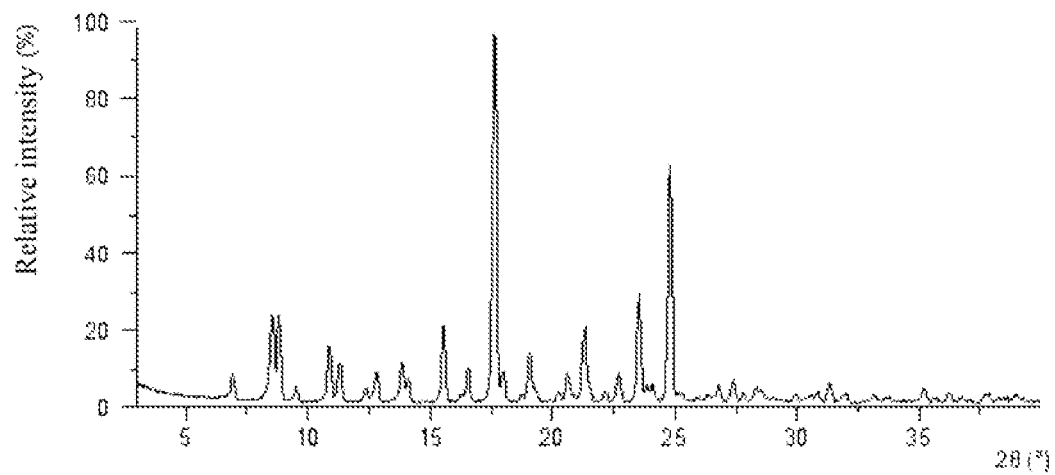
FIG. 1 is an XRPD pattern of Cu-Kα radiation of a crystal form A of a compound of formula (I).

In order to better understand the content of the present disclosure, the following specific examples are used for further description, but the specific embodiments do not limit the content of the present disclosure.

Example 1: Preparation of a Crystal Form A of a Compound of Formula (I)

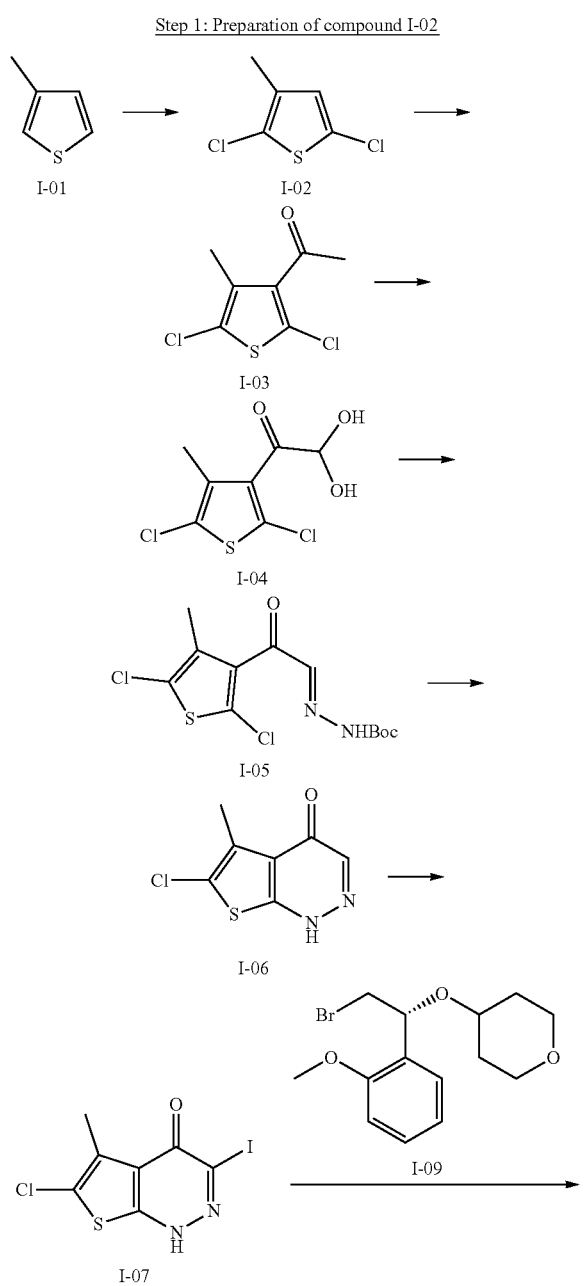

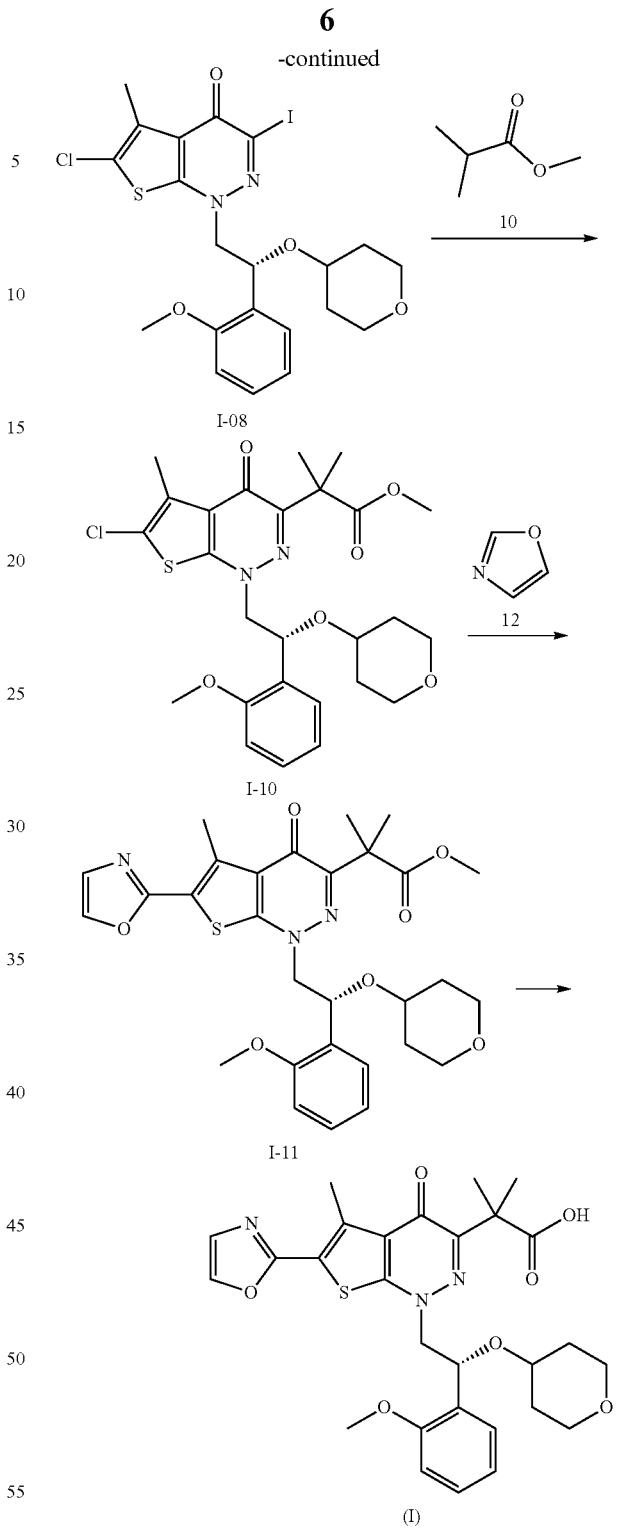

At 20° C., a raw material I-01 (650 g, 6.62 mol) and DCM (1.5 L) were added to a dry three-necked flask. The temperature was cooled down to 0° C., and SO$_2$Cl$_2$ (1.88 kg, 13.90 mol) was added dropwise rapidly for about 1 hour, the temperature was kept at 0° C. to 10° C. Once the dropwise addition was completed, the mixture was stirred at 15° C. to 20° C. for additional 16 hours (during the dropwise addition, the solution gradually turned black, gas continued to emerge, and an aqueous sodium hydroxide solution was used to absorb the exhausted gas). The reaction solution was concentrated under reduced pressure at 40° C. to obtain crude product I-02 as a yellow liquid, which was directly used in the next step. $^1$H NMR (400 MHz, CDCl$_3$) δ 6.62 (s, 1H), 2.13 (s, 3H).

Step 2: Preparation of Compound I-03

Compound I-02 (500 g, 2.99 mol), AcCl (481.6 g, 2.05 eq) and DCM (2.5 L) were added to a dry 5 L three-necked flask, and the temperature was cooled down to 0° C. Then AlCl$_3$ (478.4 g, 3.59 mol) was added in batches (about 100 g per batch), and the internal temperature was controlled at 0° C. to 10° C., with the addition completed over about 1 hour. The reaction system was slowly warmed to 20° C., and stirred for additional 12 hours. The reaction solution was slowly poured onto about 2 kg of crushed ice for quenching, and stirred while pouring to keep a large amount of crushed ice always present in the system. After the ice was completely melted, the liquid was separated. The aqueous phase was extracted with DCM (500 mL×2). The combined organic phase was washed with water (1 L×2) and brine (1 L×2), dried over anhydrous sodium sulfate, and concentrated under reduced pressure to obtain product I-03 as a yellow liquid. $^1$H NMR (400 MHz, CDCl$_3$) δ 2.53 (s, 3H), 2.15 (s, 3H).

Step 3: Preparation of Compound I-04

At 20° C., the raw material I-03 (500 g, 2.39 mol) and DMSO (2.5 L) were added to a dry 5 L three-necked flask, and then aq. HBr (1.45 kg, 7.17 mol) was added dropwise rapidly, with the dropwise addition completed over about 1 hour (during the dropwise addition, the temperature increased, and the temperature of the system was warmed to 52° C.). The mixture was slowly warmed to 60° C., and stirred for additional 12 hours. The reaction solution was slowly poured into about 5 kg of crushed ice for quenching, and petroleum ether (1.5 L) was added. The mixture was rapidly stirred for about 20 minutes until a large amount of yellow solid was precipitated, and filtered. The filter cake was washed with petroleum ether (500 mL×3), and then drained off under reduced pressure to obtain product I-04 as a yellow solid. The crude product was directly used in the next step.

Step 4: Preparation of Compound I-05

At 20° C., the raw material I-04 (300 g, 1.25 mol) and 2-MeTHF (3 L) were added to a dry 5 L three-necked flask, and then HOAc (75 g, 1.25 mol) and BocNHNH$_2$ (165.2 g, 1.25 mol) were added. The mixture was stirred for additional 16 hours. The reaction solution was washed successively with water (1 L), 20% aqueous potassium carbonate solution (500 mL×2) and brine (1 L×2), dried over anhydrous sodium sulfate, and concentrated under reduced pressure to obtain product I-05 as a black oily liquid. The crude product was directly used in the next step.

Step 5: Preparation of Compound I-06

At 20° C., the raw material I-05 (560 g, 1.66 mol) and DMSO (2.5 L) were added to a dry 5 L three-necked flask, and then K$_2$CO$_3$ (229.5 g, 1.66 mol) was added. The mixture was warmed to 100° C., and stirred for 16 hours. The reaction solution was cooled down to room temperature, and then poured into a mixed solution of water (4 L) and petroleum ether/ethyl acetate (4/1, 1 L). The mixture was stirred for 5 minutes, then adjusted pH to 3 with a saturated aqueous potassium bisulfate solution until a sandy solid was precipitated, and filtered to obtain crude product as a black solid. The crude product as a black solid was stirred with acetonitrile (1 L) at room temperature for additional 1 hour to obtain product I-06 as a brown solid. The crude product was directly used in the next step. $^1$H NMR (400 MHz, d$_6$-DMSO) δ 2.47 (s, 3H).

Step 6: Preparation of Compound I-07

At 20° C., the raw material I-06 (3.0 kg, 15.0 mol) and DMF (15 L) were added to a dry 50 L reaction kettle, and then NIS (2.5 kg, 11.1 mol) was added in batches (250 g per batch). Once the feeding was completed, the reaction mixture was warmed to 50° C., and stirred for 1.5 hours. The reaction solution was cooled down to room temperature, and then poured into 45 L of an aqueous solution in which 500 g of sodium bisulfite was dissolved. The mixture was stirred for 5 minutes until a brown solid was precipitated, and filtered to obtain a brown crude product. The brown crude product was stirred with acetonitrile (15 L) at room temperature for 1 hour, and filtered. The filter cake was dried under vacuum to obtain product I-07 as a brown solid. The crude product was directly used in the next step. $^1$H NMR (400 MHz, d$_6$-DMSO) δ 2.47 (s, 3H).

Step 7: Preparation of Compound I-08

At 20° C., DMF (25 L) was added to a dry 50 L jacketed kettle, and stirring was started. Then the raw materials I-07 (5.2 kg, 15.9 mol) and I-09 (4.0 kg, 12.7 mol) and K$_2$CO$_3$ (1.75 kg, 12.7 mol) were added. Once the feeding was completed, the mixture was warmed to 115° C., and stirred for 24 hours. The reaction mixture was cooled down to room temperature. The reaction solution was combined with another batch (from 4.5 kg of the raw material I-07) and then processed. The combined reaction solution was added to a mixed solution of water (37.5 L) and ethyl acetate (8 L) until a solid was precipitated, and filtered. The filtrate was separated, and the aqueous phase was extracted with ethyl acetate (8 L×2). The organic phase was combined, dried over anhydrous sodium sulfate, filtered, and concentrated under increased pressure to obtain a residue. The filter cake and the concentrated residue were combined, and methanol (15 L) was added. The mixture was stirred at room temperature for 1 hour, and then filtered. The filtrate was concentrated under reduced pressure, and n-heptane (5 L) was added to the residue, followed by stirring for 1 hour. The n-heptane was poured out, and tert-butyl methyl ether (4 L) was added. The mixture was heated to 60° C., stirred rapidly for 0.5 hour, then cooled down to 25° C., stirred for additional 1 hour, and then filtered. All filter cakes were combined and dried under vacuum at 40° C. to obtain product I-08 as a yellow solid. $^1$H NMR (400 MHz, d$_6$-DMSO) δ 7.48-7.46 (m, 1H), 7.36-7.33 (m, 1H), 7.07-7.02 (m, 2H), 5.30 (dd, J=9.2, 3.6 Hz, 1H), 4.41 (dd, J=14.4, 3.6 Hz, 1H), 4.17 (dd, J=14.4, 9.2 Hz, 1H), 3.85 (s, 3H), 3.38-3.36 (m, 1H), 3.35-3.24 (m, 2H), 3.24-3.14 (m, 2H), 2.45 (s, 3H), 1.63-1.62 (m, 1H), 1.56-1.54 (m, 1H), 1.34-1.31 (m, 1H), 1.05-1.00 (m, 1H).

Step 8: Preparation of Compound I-10

Reagents toluene (22 L) and dicyclohexylamine (1422.0 mL, 2 eq) were added to a 50 L reaction kettle. The reaction mixture was bubbled with nitrogen for 5 minutes, and the temperature of the reaction kettle was adjusted to −10° C. to 5° C. Under nitrogen protection, butyllithium (2.86 L, 2 eq) was slowly added dropwise to the reaction solution (with the internal temperature controlled at −10° C. to 5° C.), the internal temperature of the reaction solution was controlled at −10° C. to 5° C., and the reaction solution was stirred for 50 to 70 minutes. Then under nitrogen protection, methyl isobutyrate (817.2 mL, 2 eq) was slowly added dropwise to the reaction solution (with the internal temperature controlled at −10° C. to 5° C.), the internal temperature of the reaction solution was controlled at −10° C. to 5° C., and the reaction solution was stirred for 50 to 70 minutes. Under nitrogen bubbling, I-08 (2001.6 g, 1 eq) was added to the reaction solution, and then under nitrogen protection, $Pd_2(dba)_3$ (32.4 g, 0.01 eq) and $PtBu_3$ (10% toluene solution, 251.6 mL, 0.03 eq) were added to the reaction solution. The reaction solution was slowly warmed to 20° C., and then stirred at 20° C. for 50 to 70 minutes.

Water (8 L) was added to the reaction solution, and the aqueous phase was separated by liquid separation. Then, an aqueous hydrochloric acid solution (3 M, 5 L) was slowly added to the reaction solution to adjust pH to about 4 to 5, and the mixture was filtered through celite. The filter cake was washed with ethyl acetate (15 L). The filtrate was left to stand for layering, and the aqueous phase was separated. The organic phase was washed with an aqueous hydrochloric acid solution (1 M, 10 L), and then an aqueous potassium carbonate solution (0.2 M, 10 L). The aqueous phase was separated, and filtered through celite since there were a large amount of floccule-containing products in the aqueous phase. The filter cake was washed with ethyl acetate (10 L), and the aqueous phase was separated by liquid separation. The organic phase was combined, washed with a saturated aqueous sodium chloride solution (15 L), and concentrated under reduced pressure to obtain a crude product of this batch (according to this method, 2 kg and 1.4 kg of the materials were added to additional batches of reactions, which were subjected to post-processing respectively to obtain crude products). All batches of crude products were combined, and separated and purified by silica gel column chromatography (n-heptane:ethyl acetate=10:1 to 3:1) using ethyl acetate and n-heptane as eluents to obtain a yellow solid I-10. LCMS: [M+H]$^+$=431.3, $^1$HNMR (400 MHz, CDCl$_3$) δ ppm 7.51 (dd, J=7.6, 1.6 Hz, 1H), 7.36-7.32 (m, 1H), 7.05-7.02 (m, 1H), 6.91 (d, J=8.0 Hz, 1H), 5.44 (dd, J=8.8, 3.2 Hz, 1H), 4.35 (dd, J=14.0, 3.2 Hz, 1H), 4.06 (dd, J=14.0, 8.8 Hz, 1H), 3.87 (s, 3H), 3.80-3.74 (m, 1H), 3.68 (s, 3H), 3.58-3.52 (m, 1H), 3.43-3.23 (m, 3H), 2.56 (s, 3H), 1.76-1.72 (m, 1H), 1.60-1.45 (m, 8H), 1.28-1.20 (m, 1H).

Step 9: Preparation of Compound I-11

2-Methyltetrahydrofuran (1 L) and oxazole (96.0 mL, 4.0 eq) were successively added to a 10 L three-necked reaction flask, and the mixture was bubbled with nitrogen for 5 minutes. The temperature in the reaction flask was adjusted to −30° C. to −15° C. Under nitrogen protection, TMPMgCl·LiCl (1.8 L, 4.8 eq) was slowly added dropwise to the reaction solution (with the internal temperature controlled at −30° C. to −15° C.), the internal temperature of the reaction solution was controlled at −30° C. to −15° C., and the reaction solution was stirred for 30 to 40 minutes. Then under nitrogen protection, $ZnCl_2$ (1.5 L, 8 eq) was slowly added dropwise to the reaction solution (with the internal temperature controlled at −30° C. to −15° C.). Once the dropwise addition was completed, the cooling bath was removed, and the reaction solution was stirred and slowly warmed to 15° C. to 20° C. to obtain a zinc reagent of oxazole.

2-Methyltetrahydrofuran (2 L) and an intermediate I-10 (200 g) were successively added to another 10 L three-necked reaction flask, and the mixture was bubbled with nitrogen for 5 minutes. Under nitrogen protection, $Pd_2(dba)_3$ (34.6 g, 0.1 eq) and RuPhos (34.9 g, 0.3 eq) were added to the reaction flask, and then the reaction solution was warmed to 60° C. to 70° C., and stirred for 30 to 50 minutes. Then the zinc reagent of oxazole was added to the reaction solution, and the reaction solution was warmed to 90° C. to 95° C., and stirred at this temperature for additional 13 to 16 hours.

Five pots of parallel reactions were combined and then processed. The reaction solution was cooled down to room temperature, and then added to an aqueous hydrochloric acid solution (1 M, 20 L, 0° C. to 5° C.) to adjust pH to 3 to 4. The aqueous phase was separated by liquid separation, and extracted with ethyl acetate (5 L). The organic phase was combined, washed with a saturated aqueous sodium chloride solution (10 L×2), and concentrated under reduced pressure to obtain a crude product (according to this method, additional 15 pots of reactions (200 g of the material was added to each reaction) were divided into three batches and then processed, with 1 kg per batch, to obtain crude products), which was separated and purified by silica gel column chromatography. The purified solid was added to isopropanol (4 L). The mixture was warmed to 50° C. to 55° C., stirred until the solid was completely dissolved, and stirred for additional 30 to 40 minutes. Then the mixture was naturally cooled down to 25° C. to 30° C., and stirred for 2.0 to 2.5 hours. n-Heptane (4 L) was added to the reaction solution, and stirred at 25° C. to 30° C. for 12 to 13 hours, followed by filtration. The filter cake was rinsed with n-heptane (2 L), then drained off, and concentrated under reduced pressure to obtain a yellow solid I-11. LCMS: [M+H]$^+$=568.3, $^1$HNMR (400 MHz, CDCl$_3$) δ ppm 7.75 (s, 1H), 7.54 (dd, J=7.6, 1.2 Hz, 1H), 7.33 (td, J=7.8, 1.6 Hz, 1H), 7.26 (s, 1H), 7.06-7.04 (m, 1H), 6.91 (d, J=8.0 Hz, 1H), 5.49 (dd, J=8.8, 3.2 Hz, 1H), 4.41 (dd, J=14.0, 3.2 Hz, 1H), 4.17 (dd, J=14.0, 8.8 Hz, 1H), 3.87 (s, 3H), 4.23-4.12 (m, 1H), 3.78-3.71 (m, 1H), 3.70 (s, 3H), 3.56-3.49 (m, 1H), 3.45-3.21 (m, 3H), 3.00 (s, 3H), 1.71-1.70 (m, 1H), 1.64-1.48 (m, 8H), 1.27-1.21 (m, 1H).

Step 10: Preparation of Crude Product of Compound I

Ethanol (25 L) and intermediate I-11 were successively added to a 50 L reaction kettle, and the mixture was warmed to 55° C. to 60° C. The mixture was stirred until the solid was completely dissolved, and the prepared solution of NaOH (1091.1 g) in water (5 L) was added to the reaction kettle. The reaction kettle was warmed to 70° C. to 80° C., and stirred at this temperature for additional 17 to 19 hours.

The reaction solution was cooled down to room temperature, and concentrated under reduced pressure to remove ethanol. Then the pH of the reaction solution was adjusted to 2 to 3 with a 3 M aqueous hydrochloric acid solution (10 L) (during the adjustment, the internal temperature was 15° C. to 25° C.), and filtered. To the crude product obtained by filtration was added a 0.3 M hydrochloric acid deionized water solution (10 L). The mixture was stirred at 25° C. to 30° C. for 50 to 60 minutes, and filtered. Ethanol (2 L) was added to the solid obtained by filtration, and the resulting mixture was stirred for 15 to 20 minutes, and then filtered again. The solid obtained by filtration was concentrated under reduced pressure to obtain crude product of compound of formula (I) as an off-white solid. LCMS: [M+H]$^+$=554.3, $^1$HNMR (400 MHz, CDCl$_3$) δ ppm 7.76 (s, 1H), 7.53 (dd, J=7.6, 1.6 Hz, 1H), 7.37-7.30 (m, 1H), 7.27 (s, 1H), 7.06-7.02 (m, 1H), 6.90 (d, J=8.0 Hz, 1H), 5.49 (dd, J=8.8, 4.0 Hz, 1H), 4.44 (dd, J=14.0, 4.0 Hz, 1H), 4.21 (dd, J=14.0, 8.8 Hz, 1H), 3.86 (s, 3H), 3.79-3.70 (m, 1H), 3.61-3.49 (m, 1H), 3.47-3.20 (m, 3H), 3.02 (s, 3H), 1.74-1.70 (m, 1H), 1.63-1.50 (m, 8H), 1.28-1.20 (m, 1H).

Step 11: Preparation of Crystal Form A of Compound of Formula (I)

Ethanol (2.5 L) and the crude product of the compound of formula (I) (850.0 g) were successively added to a 10 L three-necked reaction flask, and then the reaction solution was heated to 75° C. to 80° C., stirred for 30 to 35 minutes, then naturally cooled down to room temperature (25° C. to 30° C.), and filtered. The filter cake was washed with ethanol (300 mL×4), and concentrated under reduced pressure to obtain a solid, which was dried under vacuum to constant weight to obtain crystal form A of the compound of formula (I). LCMS: [M+H]$^+$=554.2, $^1$HNMR (400 MHz, CDCl$_3$) δ ppm 7.76 (d, J=0.8 Hz, 1H), 7.53 (dd, J=7.2, 1.2 Hz, 1H), 7.35-7.31 (m, 1H), 7.27 (s, 1H), 7.06-7.02 (m, J=7.2 Hz, 1H), 6.90 (d, J=8.0 Hz, 1H), 5.49 (dd, J=8.8, 4.0 Hz, 1H), 4.44 (dd, J=14.0, 4.0 Hz, 1H), 4.21 (dd, J=14.0, 8.8 Hz, 1H), 3.86 (s, 3H), 3.79-3.70 (m, 1H), 3.59-3.49 (m, 1H), 3.44-3.20 (m, 3H), 3.02 (s, 3H), 1.74-1.69 (m, 1H), 1.64-1.50 (m, 8H), 1.30-1.19 (m, 1H).

Example 2: Physical Stability Test of a Crystal Form A, as a Solid, Under Various Temperature, Humidity and Light Conditions In order to evaluate the solid stability of a crystal form A, the influencing factors (high temperature, high humidity and light), accelerated stability conditions and intermediate stability conditions were investigated for the crystal form A.

The crystal form A was placed under high temperature (60° C., closed dish) and high humidity (room temperature, 92.5% RH (relative humidity), wrapped in a parafilm with 5 to 10 small holes) for 5 days and 10 days. According to ICH conditions (visible illuminance reached 1.2E06 Lux·hrs, and ultraviolet illuminance reached 200 W·hrs/m$^2$), the crystal form A was placed under visible light and ultraviolet light (the shading control group was wrapped in tin foil) in closed dish, and meanwhile, the crystal form A was placed under accelerated stability conditions (60° C./75% RH, wrapped in a parafilm with 5 to 10 small holes) for 1 and 2 months, and under intermediate stability conditions (40° C./75% RH, wrapped in a parafilm with 5 to 10 small holes) for 1, 2 and 3 months. The samples after placement were characterized by XRPD to detect the change of the crystal form. The results show that the crystal form A remains unchanged under all stability conditions.

Experimental Example 1: In Vitro Evaluation

Experimental Objective:
To evaluate the ability of a test compound to inhibit acetyl-CoA carboxylase (ACC) by determining the IC50 value.
Experimental Materials:
1. Proteins: human acetyl-CoA carboxylase 1 (hACC1) and human acetyl-CoA carboxylase 2 (hACC2).
2. Substrate: NaHCO$_3$
3. Cofactors: acetyl-CoA and ATP (adenosine triphosphate)
4. Activator: potassium citrate
Experimental Method:
1. One-fold enzyme/substrate/cofactor was added to microwells of a well plate.
2. According to an Acoustic technique, a solution of a compound in DMSO was added to the enzyme mixture, and the resulting mixture was pre-incubated for 15 minutes.
3. ATP was added thereto to initiate the reaction, and the mixture was shaken uniformly.
4. The mixture was incubated for 1 hour at room temperature.
5. The reaction was quenched, and then incubated for additional 40 minutes.
6. A detection reagent was added and the resulting mixture was incubated for 30 minutes.
7. Fluorescence was tested.
8. Data analysis was performed: based on the standard curve of ADP, the fluorescence signal was converted to the ADP product concentration and the enzyme activity was calculated. The curve was fitted using Graphpad Prism software to obtain the IC50 value. The experimental results are as shown in Table 2.

TABLE 2

Results of in vitro screening tests of the compound of the present disclosure

| Compound | hACC1 (nM) | hACC2 (nM) |
| --- | --- | --- |
| Compound of formula (I) | 14.1 | 10.3 |

Conclusion: The compound of the present disclosure has strong inhibitory activity on human ACC1/ACC2 enzyme.

Experimental Example 2: Pharmacokinetic Evaluation of a Compound

Experimental Objective:
To test the pharmacokinetics of the compound in C57BL/6 mice Experimental materials:
C57BL/6 mice (male, 18 to 30 g, 7 to 9 weeks old, Shanghai Lingchang Biotechnology Co., Ltd.)
Experimental Operations:
A clear solution of a test compound (0.5 mg/ml, 10% DMSO, 10% polyethylene glycol stearate, and 80% water) was injected via tail veins into 4 male C57BL/6 mice (overnight fasting, 7 to 9 weeks old), at a dose of 2.0 mg/kg. A suspension of the test compound or the clear solution thereof (1 mg/ml, 10% PEG400, 90% (0.5% methylcellulose+0.2% Tween 80)) was administered by gavage to 4 male C57BL/6 mice (overnight fasting, 7 to 9 weeks old), at a dose of 10 mg/kg.

Two mice were set in a group and subjected to blood sampling alternatively, with 4 to 5 blood sampling time points per mouse. At 0.0833 h (IV group only), 0.25 h, 0.5 h, 1.0 h, 2.0 h, 4.0 h, 6.0 h, 8.0 h, and 24 h after the mice were administered intravenously or by gavage, about 30 μL of blood was collected by saphenous vein puncture and placed in an anticoagulation tube supplemented with EDTA-K2, and the plasma was separated by centrifugation. The LC-MS/MS method was used to determine the blood drug concentration, and the WinNonlin™ Version 6.3 (Pharsight, Mountain View, Calif.) pharmacokinetic software was used to calculate the relevant pharmacokinetic parameters by the non-compartmental model linear logarithmic trapezoidal method.

The experimental results are as shown in Table 3:

TABLE 3

Pharmacokinetic test results

| Sample to be tested | Clearance rate (mL/min/kg) | Half-life $T_{1/2}$ (h) | Concentration integral AUC (nM · hr) | Bioavailability F (%) |
|---|---|---|---|---|
| Compound of formula (I) | 27.3 | 1.85 | 7211 | 66.7 |

Conclusion: The compound of formula (I) of the present disclosure can significantly improve a single indicator or partial indicators of pharmacokinetics in mice.

Experimental Example 3: In Vivo Pharmacodynamic Study in an HFD+CCl4-Induced NASH Mouse Model Experimental Objective:

To study the effect of a compound on improving NASH and liver fibrosis in an HFD+CCl$_4$ mouse model, with I-181 as a reference compound.

I-181 is an acetyl-CoA carboxylase inhibitor and is currently undergoing a phase II clinical study on non-alcoholic fatty liver disease (NAFLD). The HFD+CCl$_4$ mouse model used in this study is an animal model that simulates human non-alcoholic fatty liver disease evolving into NASH. High-fat diet leads to fat accumulation and steatosis in liver cells; CCl$_4$ (intraperitoneal injection, twice a week) simulates the "second hit" of liver injury. This model is stable and reliable, and has high similarity to the pathogenesis of human NASH; moreover, it has the main pathological characteristics of NASH, including steatosis, apoptosis, inflammation and fibrosis, and also shows an increase in levels of plasma aminotransferases (ALT and AST).

Experimental Design:

The modeling for this experiment included two steps: high-fat diet feeding and CCl$_4$ induction. Firstly, the mice were fed with high-fat diet to induce non-alcoholic fatty liver, and the mice weighing more than (>) 38 g were selected and continuously fed with high-fat diet, accompanied by the intraperitoneal injection of 25% CCl$_4$ (0.5 mg/kg, twice a week, for a total of four weeks). The day of starting CCl$_4$ administration was set as day 0, and the time of starting CCl$_4$ administration was set as hour 0. On the day of starting CCl$_4$ administration, the administration by gavage was started, and the administration volume of each group was 5 mL/kg, once a day for 4 weeks (28 days). The injection time of CCl$_4$ should be more than 4 hours apart from the first administration time point of the day. The experiment was divided into 6 groups, i.e., the healthy control group, model group, reference compound group (GS-0976), and test compound groups (a compound of formula (I), three doses). The healthy control group consisted of 10 normal mice, which were fed with normal diet during the experiment, without CCl$_4$ injection; 50 obese mice were used in the model group and the administration groups, with 10 mice each group. After grouping, the intraperitoneal injection of CCl$_4$ was started and different doses of drugs were administered respectively. The grouping and dosage design are as shown in Table 4.

TABLE 4

Animal grouping and dosage regimen

| Group | Number of animals | Compound to be tested | Vehicle | Dosage regimen (dosage \| mode of administration \| frequency \| total duration) | Diet and CCl$_4$ injection |
|---|---|---|---|---|---|
| Healthy control group | 10 | Vehicle | 40% polyethylene glycol/10% polyethylene glycol-15 hydroxystearate/50% water | 0 \| by gavage \| QD \| day 0 to day 27 | Normal diet, without CCl$_4$ injection |
| Model group | 10 | Vehicle | 40% polyethylene glycol/10% polyethylene glycol-15 hydroxystearate/50% water | 0 \| by gavage \| QD \| day 0 to day 27 | High-fat diet, with CCl$_4$ injection |
| I-181, 3 mpk | 10 | I-181 | 40% polyethylene glycol/10% polyethylene glycol-15 hydroxystearate/50% water | 3 mg/kg \| by gavage \| QD \| day 0 to day 27 | High-fat diet, with CCl$_4$ injection |
| Compound of formula (I), 0.5 mpk | 10 | Compound of formula (I) | 40% polyethylene glycol/10% polyethylene glycol-15 hydroxystearate/50% water | 0.5 mg/kg \| Intragastric administration \| QD \| day 0 to day 27 | High-fat diet, with CCl$_4$ injection |
| Compound of formula (I), 1 mpk | 10 | Compound of formula (I) | 40% polyethylene glycol/10% polyethylene glycol-15 hydroxystearate/50% water | 1 mg/kg \| Intragastric administration \| QD \| day 0 to day 27 | High-fat diet, with CCl$_4$ injection |
| Compound of formula (I), 3 mpk | 10 | Compound of formula (I) | 40% polyethylene glycol/10% polyethylene glycol-15 hydroxystearate/50% water | 3 mg/kg \| by gavage \| QD \| day 0 to day 27 | High-fat diet, with CCl$_4$ injection |

Experimental Results:

In the mouse model induced by the combination of high-fat diet and CCl₄, the compound of formula (I) achieves the same efficacy as the reference compound at a higher dose in both dimensions of NAS and fibrosis.

What is claimed is:

1. A crystal form A of a compound of formula (I), wherein the crystal form has an X-ray powder diffraction pattern comprising characteristic diffraction peaks at the following 2θ angles: 8.54±0.20°, 17.64±0.20° and 24.81±0.2°;

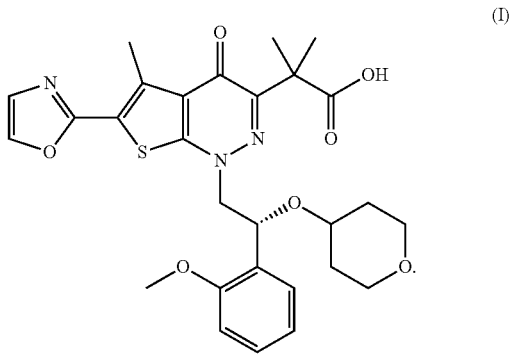 [SMILES: COc1ccccc1[C@H](Cn1nc(C(C)(C)C(=O)O)c(=O)c2c(C)c(-c3ncco3)sc21)OC1CCOCC1]

(I)

2. The crystal form A according to claim 1, wherein the crystal form has an X-ray powder diffraction pattern comprising characteristic diffraction peaks at the following 2θ angles: 8.54±0.20°, 10.87±0.20°, 15.55±0.20°, 16.56±0.20°, 17.64±0.20°, 21.32±0.20°, 23.53±0.20° and 24.81±0.20°.

3. The crystal form A according to claim 2, wherein the crystal form has an X-ray powder diffraction pattern comprising characteristic diffraction peaks at the following 2θ angles: 6.91°, 8.54°, 8.80°, 9.51°, 10.87°, 11.30°, 12.38°, 12.81°, 13.84°, 14.10°, 15.55°, 16.56°, 17.64°, 17.99°, 18.76°, 19.07°, 20.27°, 20.63°, 21.32°, 22.19°, 22.71°, 23.53°, 24.07°, 24.81°, 26.80°, 27.40°, 27.79°, 28.34°, 29.94°, 30.86°, 30.86°, 31.34°, 31.98°, 33.17°, 33.69°, 35.21°, 35.64°, 36.25°, 36.75°, 37.79° and 38.98°.

4. The crystal form A according to claim 3, wherein the crystal form has an XRPD pattern as shown in FIG. 1.

5. The crystal form A according to claim 1, wherein the crystal form has a differential scanning calorimetry curve comprising an endothermic peak with an onset at 234.9° C.

Figure 2:
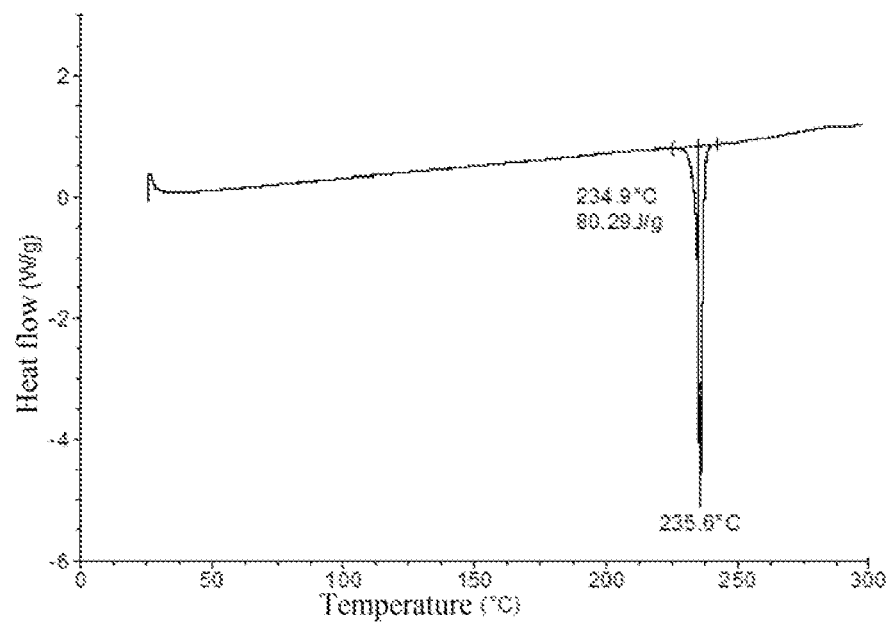
FIG. 2 is a DSC pattern of a crystal form A of a compound of formula (I).

6. The crystal form A according to claim 5, wherein the crystal form has a DSC pattern as shown in FIG. 2.

7. The crystal form A according to claim 1, wherein the crystal form has a thermal gravimetric analysis curve showing a weight loss of 0.86% at 200° C.±3° C.

Figure 3:
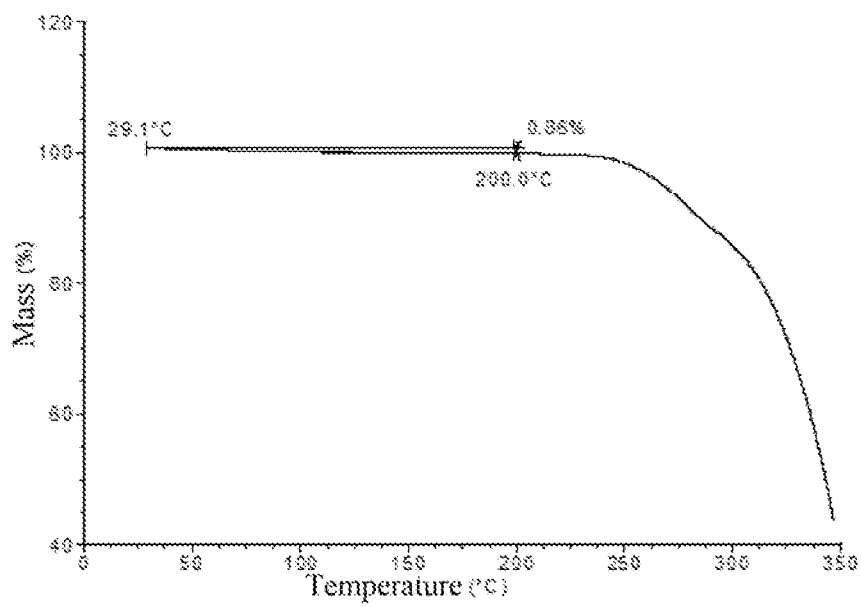
FIG. 3 is a TGA pattern of a crystal form A of a compound of formula (I).

8. The crystal form A according to claim 7, wherein the crystal form has a TGA pattern as shown in FIG. 3.

* * * * *